United States Patent [19]
Crumly et al.

[11] Patent Number: 5,364,277
[45] Date of Patent: Nov. 15, 1994

[54] THREE-DIMENSIONAL ELECTROFORMED CIRCUITRY

[75] Inventors: William R. Crumly, Anaheim; Christopher M. Schreiber, Newport Beach; Haim Feigenbaum, Irvine, all of Calif.

[73] Assignee: Hughes Aircraft Company, Los Angeles, Calif.

[21] Appl. No.: 106,975

[22] Filed: Aug. 16, 1993

Related U.S. Application Data

[60] Continuation of Ser. No. 849,849, Mar. 12, 1992, abandoned, which is a division of Ser. No. 580,759, Sep. 11, 1990, Pat. No. 5,197,184.

[51] Int. Cl.$^5$ .............................................. H01R 9/09
[52] U.S. Cl. ........................................ 439/67; 439/74
[58] Field of Search ............... 439/67, 77, 74, 492, 439/493

[56] References Cited

U.S. PATENT DOCUMENTS

| | | | |
|---|---|---|---|
| 4,116,517 | 9/1978 | Selvin et al. | 439/67 |
| 4,403,272 | 9/1983 | Larson et al. | 439/85 X |
| 4,891,014 | 1/1990 | Simpson et al. | 439/67 |
| 4,911,643 | 3/1990 | Perry et al. | 439/67 |
| 5,147,208 | 9/1992 | Bachler | 439/77 X |

FOREIGN PATENT DOCUMENTS

| | | |
|---|---|---|
| 51-104570 | 9/1976 | Japan . |
| 59-197191 | 11/1984 | Japan . |
| 63-45888 | 2/1988 | Japan . |

Primary Examiner—Khiem Nguyen
Attorney, Agent, or Firm—Elizabeth E. Leitereg; T. Gudmestad; W. K. Denson-Low

[57] ABSTRACT

A pressure-type contact for flexible or conventional wire cable terminations is fabricated from electroformed thin metallic wafers (100) in which one wafer is plated with a raised conductive interconnection feature (122). The electrical circuitry (118, 120) is made on a stainless steel mandrel (10, 10a) having a Teflon pattern (16, 16a) on its surface that allows the desired electrical circuit (30, 32, 34, 30a, 32a, 34a, 78) to be electrolytically plated upon the conductive mandrel surface. The mandrel surface is formed with projecting features in the form of depressions (24, 24a) that will form a series of dots or raised interconnection features on the termination wafers. The mandrel also has projecting posts (76) for providing electrical connection through the substrate.

6 Claims, 3 Drawing Sheets

THREE-DIMENSIONAL ELECTROFORMED CIRCUITRY

This is a continuation of application Ser. No. 07/849,849, filed Mar. 12, 1992 now abandoned, which is a division of application Ser. No. 580,758, filed Sep. 11, 1990 now U.S. Pat. No. 5,197,184.

BACKGROUND OF THE INVENTION

1. Field of the Invention

The present invention relates to manufacture of electrical circuitry and, more particularly, concerns manufacture of electrical circuitry by additive electroforming processes that provide the circuitry with three-dimensional features having a three-dimensional configuration that extends in one or more directions from the plane of the circuit.

2. Description of Related Art

The ubiquitous printed circuits are being developed in ever-expanding applications and continuously varying configurations. Both flexible and rigid printed circuits are connected to similar circuits and other components by means of various types of connecting devices. Flat, flexible printed circuit connecting cables warrant use of similarly configured connecting devices and have been developed to a point where connection between one such printed circuit cable and another circuit is made by providing a plurality of projecting metallic interconnection features that may be pressed against either similar features or mating metallic connecting pads on the other circuit component or components. Flexible circuit terminations or connecting wafers of this type are described in U.S. Pat. No. 4,125,310 to Patrick A. Reardon, II; U.S. Pat. No. 4,116,517 to Selvane, et al.; and U.S. Pat. No. 4,453,795 to Moulin, et al. The connectors of these patents embody a substrate having traces chemically milled thereon with a plurality of metallic raised features later formed to project from the plane of the circuit conductors. Thus, when two such connectors are placed face to face, with the raised features of one in registration and contact with the other, the planes of the etched electrical circuits are suitably spaced from one another because of the projection of the features. The two circuits may be physically clamped together to press the features against one another, thereby making firm and intimate electrical contact between the two circuits.

These termination arrangements are effective and reliable in operation but difficult, costly and time consuming to manufacture. Major problems in manufacture of such connectors derive from the fact that the projecting contact buttons must be fabricated separately from (either before or after) the fabrication of the circuitry itself. This creates difficult registration problems. For example, after drilling appropriate interconnection and tooling holes through a copper clad dielectric core or substrate and plating through some of the holes to interconnect circuitry on the two sides of the core, the core is placed between the circuit artwork (optical masks) positioned on either side of the core and the holes in the artwork or datum points are then manually aligned with the predrilled holes in the core. Where dozens of parts may be made on a single panel that is 12"×18", and alignment tolerances are measured within a few microns, registration of all or even most holes in all of the parts is exceedingly difficult, time consuming and often times not possible because of changes in dimensions of the panels that occur during some of the processing. After registration of the artwork, the substantially planar circuitry is chemically milled or etched on the copper surfaces (the panel may often be covered with a coating of copper on both sides for a double sided panel). The etching process involves application of photoresist, masking the resist, exposing the resist, developing the resist, then etching through the portions of the copper not protected by the resist so that upon stripping of the remaining resist, the circuit pattern of the copper conductors remains.

Where raised interconnection features are employed as in flexible circuit termination wafers, it is then necessary to plate the projecting contact features on pads formed in the circuitry which has been previously etched. These features must be precisely registered with the selected pads and with the datum of the panel. However, the panels have been previously processed to form the circuit traces so that further stresses occurring in such processing effect changes in dimension (usually, but not always, shrinkage). The changing dimensions cause severe registration problems. To manufacture the projecting contact features (sometimes called "dots"), the etched circuit is coated with a resist. Again, the appropriate artwork for defining the desired hole in the resist at the dot location must be carefully registered, which is now an even more difficult task.

In some cases, the projecting interconnection features or dots may be formed first, before the remainder of the etched circuit is formed. But, in any event, the feature must be formed separately, at a different time than the time of forming the etched circuitry, and thus the registration problems are created or exacerbated.

In such circuits, where a connection must be made from circuitry on one side of the core to circuitry on the other side of the core, holes are drilled and throughhole plated, requiring still further steps and creating other registration problems that increase the cost and time of manufacture.

Conventional etched circuit processes, in general, have a number of disadvantages. Dimensional precision is difficult to achieve. The use of various etching, stripping and cleaning fluids requires special handling of hazardous chemicals. Techniques for disposal of the resulting effluents are complex and expensive, and subject to strict government controls. Etched circuit processing has a relatively low yield, greatly increasing the cost of the processing, which inherently involves a large number of costly processing steps.

Accordingly, it is an object of the present invention to provide methods and apparatus for manufacture of electrical three-dimensional circuitry which avoid or minimize above mentioned problems, and which eliminate sequential etching and plating processes employed in the formation of three-dimensional circuitry.

SUMMARY OF THE INVENTION

In carrying out principles of the present invention, and in accordance with a preferred embodiment thereof, three-dimensional electrical circuitry is made by fully additive processes employing a circuit mandrel. The mandrel comprises a substrate having a working surface formed of a material on which can be electroformed an electrically conductive element, with the mandrel having a first feature projecting in directions perpendicular to the working surface to enable a three-dimensional electrical circuit to be formed by a single electroforming operation. The mandrel bears a pattern formed of electrically non-conductive material. Thus, the entire three-dimensional circuitry of traces and raised interconnection features may be electrodeposited in a single step, all without any photolithographic or etching processes.

According to another aspect of the invention, the mandrel may have a second feature projecting from the surface in a second direction opposite the first direction so that an electrical circuit may be formed generally lying on the working surface of the mandrel and having different features projecting in mutually opposite directions from such surface.

The drawings all (except for FIG. 17) show cross sections of the parts in various stages of manufacture.

DETAILED DESCRIPTION

The methods and apparatus described herein enable manufacture of three-dimensional electrical circuitry having circuit components lying in a single plane which is generally but not necessarily a planar surface, and which circuitry also has three-dimensional features projecting from the surface in one or more directions. Importantly, the projecting features and the circuitry are all formed by additive processes such as electrolytic plating, electroless plating, electrophoretic or electrostatic coating, or other forms of electroforming or electrodeposition of conductive material. No etching is employed in the manufacture of the circuit, making it an environmentally safe process. Briefly, the circuit is manufactured by using a mandrel having a working surface formed of a material that can have conductive circuitry electroformed thereon, and which has a pattern of a material that is resistant to the electroforming process. The mandrel has three-dimensional features projecting from its working surface, which features may project in different directions. Thus, the features may include a depression formed in the surface which will produce an electroformed projecting conductive element. The mandrel may also have a post projecting outwardly of the working surface to produce an electroformed post that extends from the surface in a direction opposite to the direction of extent of the depression formed projection.

Figure 1:
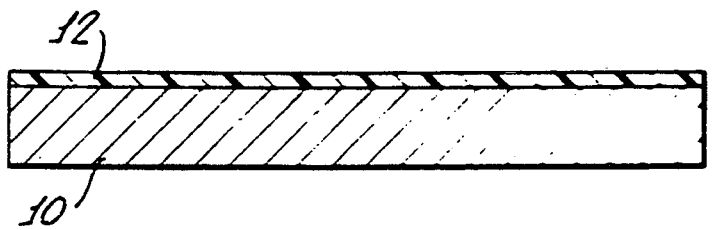
FIG. 1 illustrates a step in the formation of a mandrel.

As illustrated in cross sectional view in FIG. 1, a mandrel 10 may be formed of a sheet of a metal such as stainless steel having a thickness on the order of 1/16" for example, and having dimensions suitable for making one or a plurality of parts. Thus, for example, where a dozen parts are to be made at one time on a single 12"×18" panel, the mandrel has horizontal dimensions (in a plane perpendicular to the plane of the paper) that are suitably greater than the full dimension of the panel.

Figure 2:
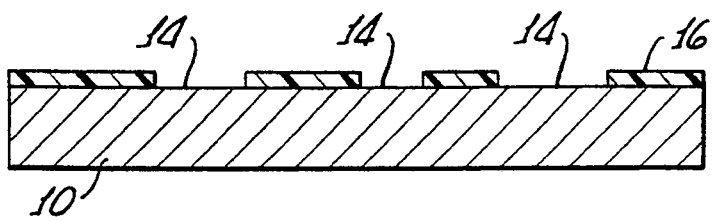
FIG. 2 illustrates a mandrel with a pattern of Teflon.
Figure 3:
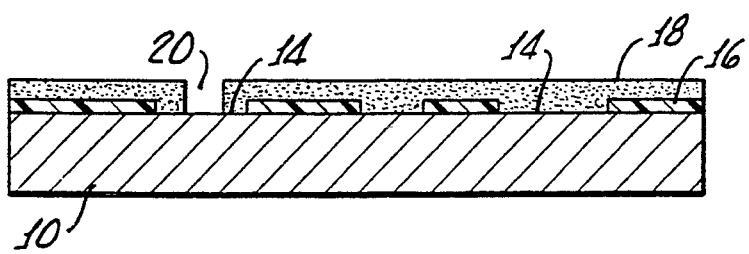
FIG. 3 shows the coating of the mandrel with resist.
Figure 4:
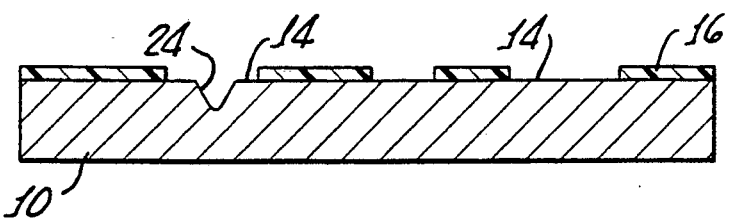
FIG. 4 shows a completed mandrel with an etched depression.

In one method to fabricate a mandrel with raised features, the stainless steel mandrel 10 is initially provided with a non-conductive coating such as Teflon 12 which is then ablated as indicated in FIG. 2, as by use of a laser, for example, to form a positive pattern of grooves such as grooves 14 in the Teflon. The pattern of grooves exposes the conductive working surface of the stainless steel mandrel and leaves a negative pattern of the electrically non-conductive Teflon 16 on the mandrel working surface. The mandrel and Teflon pattern are then coated with a suitable resist 18 as indicated in FIG. 3, which is masked, exposed and developed to leave a hole 20 in the resist 18. The resist coated mandrel is then subjected to an etching bath to form a depression 24 in the working surface 14 of the stainless steel mandrel substrate as shown in FIG. 4. The tapered configuration of depression 24 is not precisely shown in the drawings but generally denotes the effect of sideways or lateral metal removal that is inherent in the etching process. FIG. 4 illustrates the etched depression 24 with Teflon pattern 16 after resist 18 has been removed. Thus, FIG. 4 shows a completed mandrel having a single three-dimensional feature, namely the depression 24.

The mandrel of FIG. 4 will be used and reused to plate up three-dimensional electrical circuitry without any etching processes, as will now be described. Alternatively this mandrel, without its Teflon pattern, may be used as a master to replicate many working mandrels, electroformed on the master, as will be described below.

The mandrel is placed in a suitable electrolytic plating bath where electrically conductive material, such as copper, is plated onto the conductive pattern formed by the spaces 14 between the Teflon pattern elements 16, thereby providing conductive elements indicated as 30, 32 and 34, all on the same surface and forming a surface that is substantially smooth and continuous with the surface of the Teflon. The exposed surfaces of the circuit, namely those surfaces that face upwardly in the drawing of FIG. 5, may now be treated (activated) by any suitable method to enhance adhesion to a dielectric substrate that will next be laminated to the circuit elements. Such activation or treatment may include various electrochemical or mechanical known methods for roughening the copper surface for adhesion enhancement. According to an electrochemical method that has been employed, the surface is phosphatized by immersing the part in a solution of trisodium phosphate and applying an electric current to the part, which is connected as an anode or cathode. Mechanical methods include use of an abrasive slurry.

A dielectric circuit substrate or core formed of suitable material such as, for example, a one rail layer of a polyamide such as Kapton or the like coated with a one rail layer of acrylic adhesive is then laminated to the combined exposed surface of conductive elements 30, 32 and 34, and the Teflon pattern. The latter will not stick to the acrylic adhesive but, under suitable pressure and temperature such as, for example, 300 pounds per square inch at a temperature of 350° F., the acrylic, which is on the side of the core 36 that contacts the plated circuit elements 30, 32 and 34, will flow into the micro-structure in the conductive circuit and ensure optimum adhesion of the core to the conductive circuit components. Core 36 is formed with a predrilled through hole 38 for purposes to be described below.

If a connection is to be provided to an additional conductive layer on the side of the substrate opposite the circuit, this may be done while the core and circuit are still on the mandrel 10. Such a conductive layer is illustrated at 44 in FIG. 7 and may be applied by silk screening a silver epoxy or similar material in a suitable pattern on the surface 48 of the shield side of core 36. This conductive layer may also be applied by electroless or electrolytic deposition, sputtered on any combination thereof. It will be understood that the elements 30, 32, 34 are illustrated merely for purposes of exposition and that many other traces of conductive elements may be included in the described circuitry.

Figure 10:
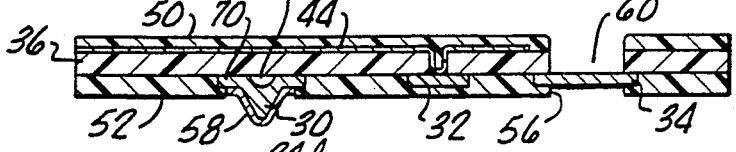
FIG. 10 shows the ablation of a window through the substrate.

Element 32 illustrates a pad to be used for a conductor or shield connection and is aligned with the predrilled hole 38 in core 36. The screened on silver epoxy shield, when applied, is caused to flow into the predrilled hole 38 and to contact the circuit element, pad 32, so as to provide electrical contact through the core 36 from pad 32 to the outer surface or shielded surface 48 of the circuit. Additionally, windows exposing circuit features such as unsupported traces used as solder fingers may be made by blanking openings in the core prior to lamination. An example of a pre-blanked window 60 is shown in FIG. 10.

Figure 7:
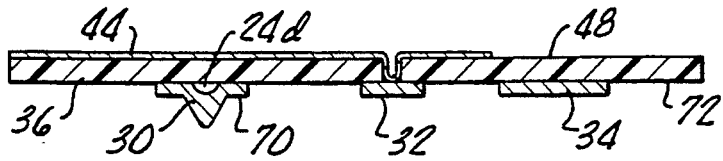
FIG. 7 illustrates the dielectric laminate separate from the mandrel and application of a ground screen on the back of the dielectric.
Figure 8:
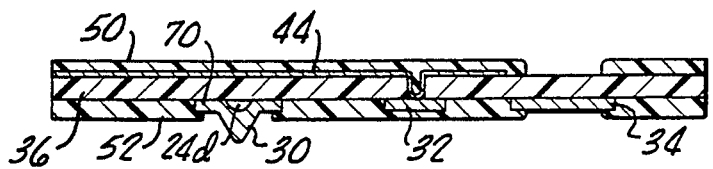
FIG. 8 illustrates application of a protective coverlay to the dielectric laminate and circuit assembly.

Either before or after application of an additional conductive layer, the core and the conductive elements 30, 32 and 34 are stripped from the mandrel. The core does not adhere to the Teflon, but its acrylic laminate provides good adhesion to the electrical conductors (which may be treated on the mandrel to promote bonding to the core) and thus the conductors are removed from the stainless steel surface which is inherently passivated (covered with an oxidation coating) so that the copper conductive elements 30, 32 and 34 may be readily stripped from the stainless steel working surface. Where the circuit and its core are thin and flexible, the circuit and core may be separated from the stainless steel by a knife or razor edge and may be flexibly lifted away from the mandrel. Where the circuit and its core are made of thicker and more rigid material, the mandrel may be made thin enough to be flexible so that stripping of the mandrel from the core and circuit may be aided by flexibility of the mandrel itself. After separation, the mandrel is free to be cleaned and reused for manufacture of another circuit. FIG. 7 illustrates a cross section of the separated circuit subassembly.

The circuit subassembly comprising core 36, conductive elements 30, 32 and 34, and the ground or shield 44 are then covered with insulation layers such as a coverlay having a portion 50 on the shield side and a portion 52 on the circuit or signal circuit side of the subassembly. The coverlay is formed with predrilled or punched holes such as hole 54 on the shield side and a registering hole 56 on the signal or circuit side, in addition to a hole that receives conductive element 30, which is a projection or contact feature 30. It may be noted at this point that registration of the predrilled coverlay with the predrilled hole of the core and with the projecting feature 30 is required, even though other registrations of tighter tolerances are largely eliminated. However, because the assembly of core and circuit elements 30, 32 and 34 has not been subjected to any etching processes, dimensions are relatively stable, and this registration poses little problem. Further, the larger tolerances allowable for holes in the coverlay with respect to other circuit components makes this registration easier to achieve than the registration typically required during the photo and etching operation that is eliminated by the process described herein.

Figure 9:
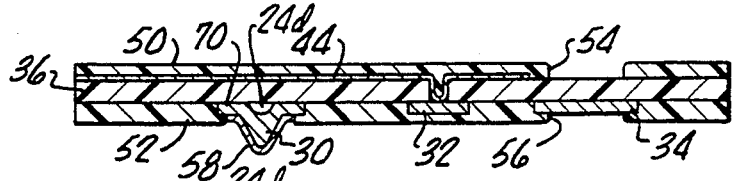
FIG. 9 illustrates gold plating of the raised feature.

The projection feature 30 is then plated with gold as shown by coating 58 of FIG. 9 and then the core 36 has a hole 60 ablated therethrough in registration with the predrilled hole 56 of the coverlay 50 so as to expose the ground plane or shield side of conductive element 34. Of course, if deemed necessary or desirable, the core 36, instead of being ablated in the step illustrated in FIG. 10 can be blanked with the hole 60. However, it is found to be more convenient and efficient to form this hole in the core through predrilled holes in the coverlay, although the laser ablation of the window 60 in the core could be carried out so that the coverlay hole 54 could be ablated at the same time so that the latter would not have to be predrilled.

Figure 11:
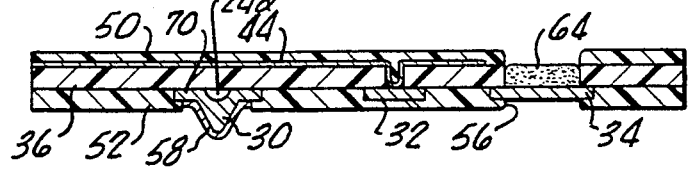
FIG. 11 illustrates the application of solder to solder fingers of the circuit assembly.

Conductive element 34 is to be employed as a solder finger to be covered with solder for the purpose of making permanent solder connections to the circuit. Accordingly, as is illustrated in FIG. 11, conductive element 34 is coated on at least one side with solder 64 and the circuit is ready to be blanked or cut out of the panel of which this circuit, together with other identical circuits, has been formed. FIG. 11 illustrates a cross section of the completed three-dimensional circuitry with its projection feature 30.

As can be seen, the entire three-dimensional circuit has been formed by additive processes without any photolithography or etching although, of course, certain features of the mandrel may be defined by etching.

The mandrel illustrated in FIG. 4 provides a core and circuit electroformed thereon wherein the circuit elements 32 and 34, in addition to the projection feature 30, all lie on the surface of the core 36 and project slightly therefrom by the thickness of the circuit elements. This configuration, of course, results from the specific configuration of the mandrel shown in FIG. 4.

Figure 12:
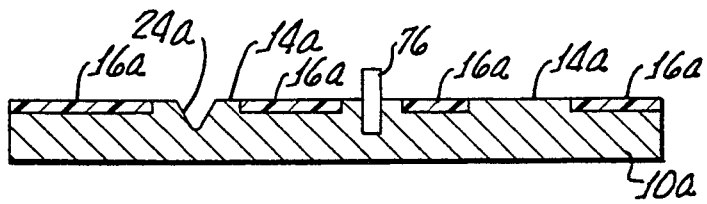
FIG. 12 illustrates an alternate form of mandrel having raised features projecting in two directions.

Formation of a circuit with embedded conductors is illustrated in FIGS. 12-16. The circuit formed by this modified process has the traces of various elements such as 32 and 34 and also the base portion 70 of projection feature 30 embedded in and flush with the lower surface 72 (see FIG. 7) of the dielectric core. In this embodiment a mandrel 10a (FIG. 12) is formed with a pattern of grooves on its surface where a Teflon pattern 16a is to be placed. Thus, the Teflon pattern 16a is formed in and flush with the working surface formed by conductive pattern 14a of the stainless steel mandrel substrate 10a. In this arrangement, after forming the grooves in the surface of the mandrel substrate to receive the Teflon, and after coating the entire surface with Teflon, the Teflon surface is lapped to remove all Teflon on surfaces 14 leaving the grooves in the mandrel filled with Teflon as illustrated in FIG. 12. Particular details of this manner of making a mandrel having Teflon filled grooves that provide a non-conductive surface that is smoothly continuous with the electrically conductive surface of the stainless steel mandrel are described in co-pending application for Apparatus and Method Using a Permanent Mandrel for Manufacture of Electrical Circuitry, Ser. No. 07/580,748, filed Sep. 11, 1990. Another method for making a mandrel useful in the practice of this invention is disclosed in a co-pending application for Laser Pattern Ablation of Fine Line Circuitry, Ser. No. 07/580,749, filed Sep. 11, 1990. The entire disclosures of both such co-pending applications, which are owned by the assignee of the present application, are incorporated by this reference as though fully set forth herein.

Figure 13:
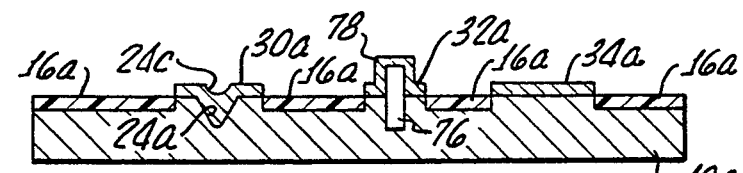
FIG. 13 illustrates electroforming of a circuit including oppositely projecting raised features.

In the mandrel of FIG. 12, after lapping the Teflon to form the smooth continuous surface of stainless steel and Teflon, the steps illustrated in FIGS. 3 and 4 are followed to etch the depression 24a in the mandrel surface. Thereafter, manufacture of the circuitry using the mandrel of FIG. 12 and the steps described in connection with FIGS. 5 through 11 is the same as described for the mandrel of FIG. 4. Alternatively, a mandrel as described above and illustrated in FIGS. 1-4 may be used to make a mandrel for making circuitry with embedded conductors by filling the grooves in the Teflon with a suitable material which will allow conductor traces to be formed on the surface (which is now coincident with the Teflon surface) and yet provide easy release. Electroplated nickel is a suitable material which forms a passivation layer allowing copper to be plated onto and released from the surface.

Where deemed necessary or desirable, to provide a second set of "raised features" or projections which project from the plane of the circuitry elements 30, 32 and 34 in a direction opposite the direction of projection of projection feature 30, a post 76 (FIG. 12) may be suitably affixed to the stainless steel mandrel substrate 10a. The post 76 may be a post plated up from the surface of mandrel 10a (or the mandrel of FIG. 4) or may be simply a short wire inserted in a hole drilled in the surface. Post 76 is made of a suitable electrically conductive material which may be steel, copper or nickel. The post will enable the circuit to be made with an electrical connection (equivalent to a plated through-the-core hole) between its signal side and its ground or shield side. Thus, the mandrel of FIG. 12 includes a stainless steel substrate 10a having a first depression 24a (forming a raised interconnection feature on the finished circuit) projecting in one direction from its working surface 14a and a second feature 76 projecting in an opposite direction from working surface 14a. The pattern 16a of electrically non-conductive material such as Teflon is coplanar with the working surface 14a, with the Teflon embedded in grooves formed in the mandrel as previously described. Like the mandrel of FIG. 4, this mandrel then may be used and reused for electroforming a desired three-dimensional circuit. Thus, as illustrated in FIG. 13, elements 30a, 32a and 34a are formed upon the mandrel by a suitable electroforming technique (as previously described) so that mandrel post 76 is now plated with a copper or other material, indicated at 78 in FIG. 13. Post 76 may be made of nickel or like material so that its surface is inherently passivated and will more readily release from the plated post portion 78.

Figure 5:
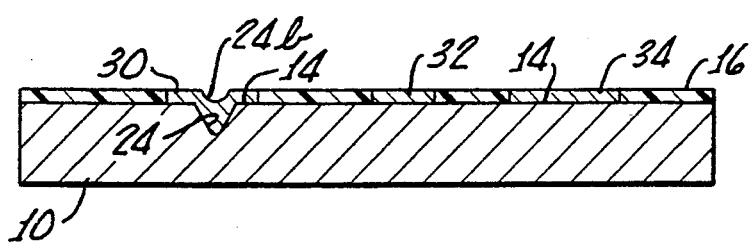
FIG. 5 shows the mandrel with a conductive circuit and raised feature electroformed thereon.

When electroforming the various conductors on the mandrel, and in particular when electroforming the depression 24a of FIGS. 12 through 16 and the corresponding depression 24 of FIGS. 1 through 11, the electroforming technique leaves a small recess in the back side of the depression, such as the recess 24b of FIG. 5 and the recess 24c of FIG. 13. When the dielectric substrate is then laminated to the conductors, a void, such as indicated at 24d in FIG. 6, may occur between the back of the depression 24 and the dielectric 36. In some arrangements this void may be acceptable and no steps may need be taken to eliminate the void. However, because of the relatively poor structural characteristics of the conductive material (which is often copper) of the raised feature, and because the very thin dielectric sheet of acrylic may be insufficient to fill the void, the raised feature may lack required structural strength to provide support required in some termination applications. Accordingly, an additional intermediate step is illustrated in the embodiment of FIGS. 12 through 16. In this intermediate step, after providing mandrel with its electrical conductors, as illustrated in FIG. 13, the recess 24c in the depression 24a is back filled with an epoxy 24e, thereby strengthening and solidifying the raised feature to provide a rigid raised feature capable of withstanding as much as 10,000 psi at 85° C. without deformation. The epoxy back fill may be applied by automated dispensers or silk screen techniques that are commonly known. Of course this step of back filling of the raised feature void may also be carried out in the process illustrated in FIGS. 1 through 11.

Figure 6:
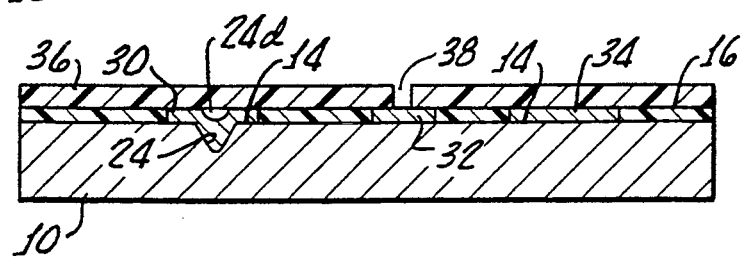
FIG. 6 shows application of a dielectric transfer laminate to the mandrel and electroformed circuit.
Figure 14:
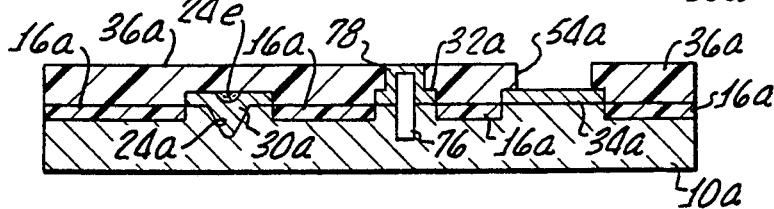
FIG. 14 illustrates the application of the dielectric core to the mandrel and circuit electroformed thereon.
Figure 15:
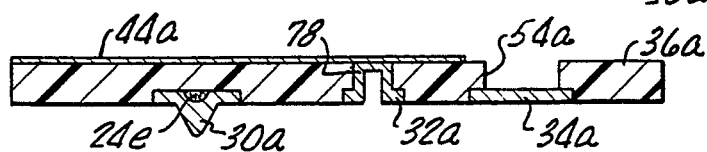
FIG. 15 illustrates the application of a silver epoxy ground or shield to one side of the core.

Now, after back filling the recess 24c with epoxy 24e, as illustrated in FIG. 14, and in a manner analogous to that illustrated and described in connection with FIG. 6, a dielectric substrate 36a is then laminated upon the mandrel with its circuit components and raised features, and either while still on the mandrel or after the core 36a and circuit components have been removed from the mandrel, a silver epoxy ground or shield 44a (FIG. 15) is screened onto the ground surface 48a of the core. It is for the purpose of making a good connection to the shield 44a on the ground side of the core from the circuit or signal side of the core that the post 78 is provided. With the arrangement illustrated in FIGS. 12 through 15, the silver epoxy 44a will readily contact the top of post 78 and does not have to be manipulated into and to the bottom of the hole 38 (see FIGS. 6 and 7) as in the prior embodiment where a ground plane hole 38 has been predrilled in the core. In the previously described arrangement of FIGS. 6 and 7, it is necessary to manipulate the applied silver epoxy through the hole in the core to form a conductive path from one side of the core to the other. In the arrangement of FIGS. 12 through 15, however, the post 78 is electroformed (plated up) together with and at the same time as the circuit and its other raised features are formed, so that the through-the-core connection is made when the circuit is made and when the conductors are formed.

Figure 16:
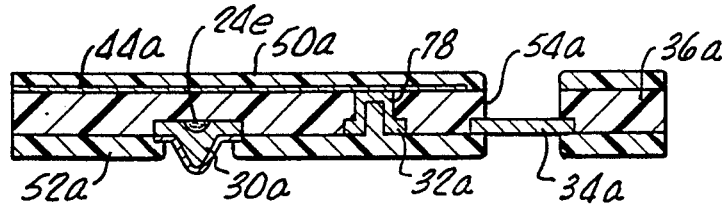
FIG. 16 illustrates the circuit assembly of FIG. 15 with its coverlay applied.

After applying the silver epoxy shield or ground plane 44a, a coverlay 50a and 52a is then provided as illustrated in FIG. 16 and a solder finger window 54a is formed in core 36a at solder finger 34a to provide the completed circuit of core and circuitry and protective coverlay shown in FIG. 16.

Figure 17:
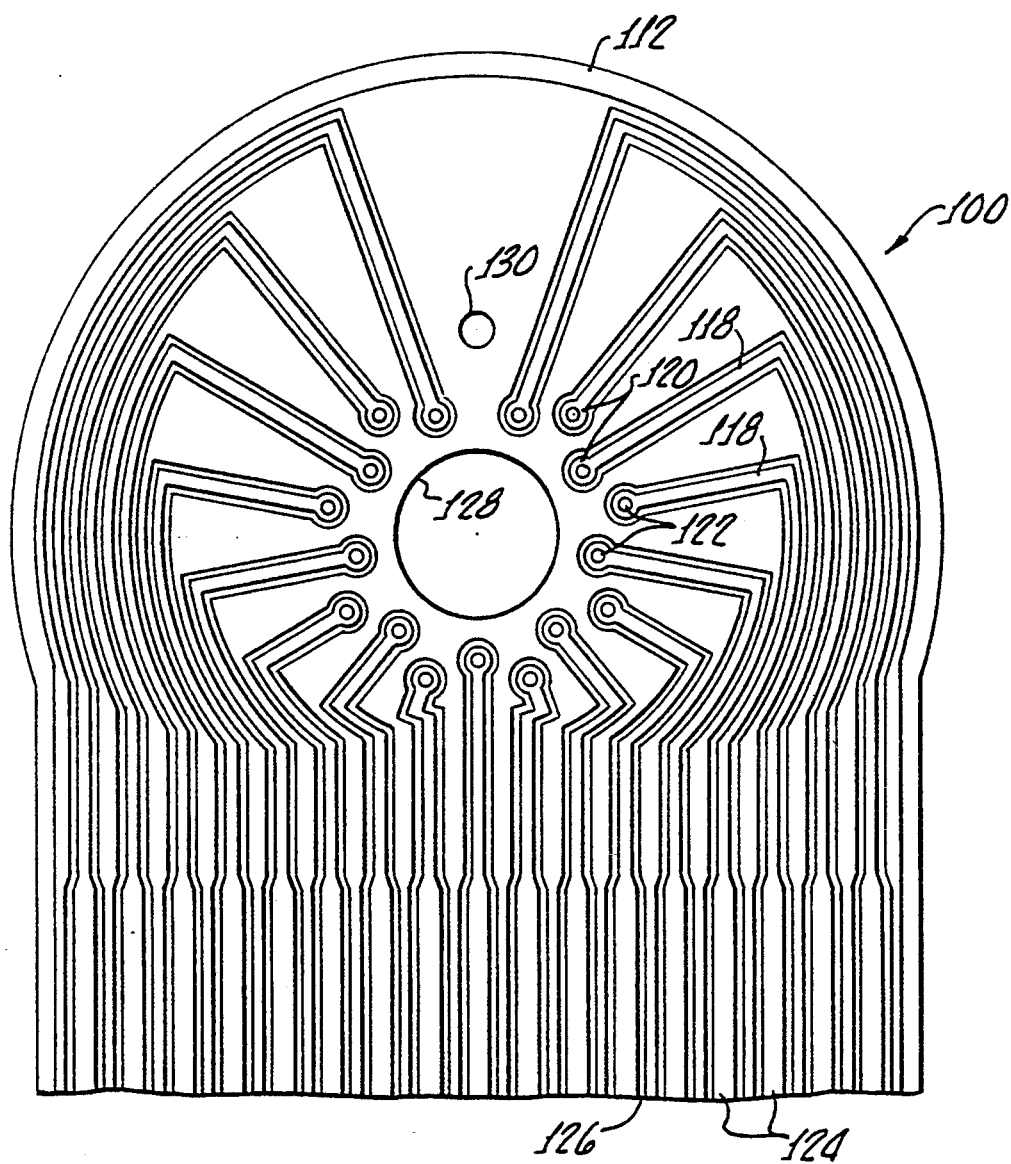
FIG. 17 illustrates a typical connection wafer.

It will be appreciated that the described circuit and methods of fabrication have applications to manufacture of many different circuit elements, whether thin and flexible or rigid circuit boards, and may be used in various types of circuits and components. The processes described herein have been initially adapted to the manufacture of flexible cable terminations of the type illustrated in the above identified patents to Moulin et al and Reardon where a group of contact buttons (raised features) is formed at the ends of conductive leads on a connection wafer for purposes of making circuit-to-circuit connections. Thus, as shown in FIG. 17 and as more particularly illustrated and described in U.S. 4,453,795 to Moulin et al, a termination wafer 100 comprises a layer or sheet of a dielectric substrate material, such as polyamide 112 having a pattern of electrically conductive traces or conductor paths 118 terminating in contact pads 120. Additionally, on one of a pair of connector wafers (only one of which is shown in FIG. 17), are formed metallic buttons (raised features) 122. The other ends 124 of conductive paths 118 extend to a common edge 126 for attachment to a flexible cable or conventional wire cable such as by surface lap soldering. Preferably a central hole 128 and an alignment hole 130 are placed through each wafer so as not only to obtain connection between a pair of wafers, but also to mutually align the respective contact pads 120 on each of the two wafers. The conductor paths 118, contact pads 120, and metallic buttons 122 are fully additively electroformed by the methods and with use of the mandrels described above. The metallic buttons 120 of FIG. 17 correspond to the contact buttons or projection features 30 of FIGS. 5–11 and 13–16 and pads 120 of FIG. 17 correspond to the pad portions 70 (see FIG. 7) of the circuitry made according to the disclosed methods and apparatus. As more particularly described in the identified U.S. Pat. No. 4,453,795, the wafer and its contact buttons 120 will be pressed against a similar wafer and contact buttons or against another electrical circuit to provide a readily connectable and disconnectable electrical interconnection of the two pads of the two terminating wafers or circuits.

It will be readily appreciated that the depressions 24 and 24a may be formed in the mandrels by various means including etching, electron discharge machining or by mechanical deformation or some combination thereof. Thus, for example, the depression in the mandrel may be made by etching to a smaller size than required and then the depression may be enlarged by punching which will provide a smoother and better finish that affords an easier release of the raised contact from the mandrel.

There have been described circuits and apparatus for the manufacture of electrical circuitry by fully additive processes requiring no etching for production of the circuit. The arrangement provides for three-dimensional circuitry having projections in one or more directions from the plane of the circuitry and employs a permanent readily reusable mandrel which may be easily cleaned for reuse after formation of each circuit.

What is claimed is:
1. An electrical circuit comprising:
  a dielectric substrate;
  a pattern of conductive traces on one side of said substrate and positioned substantially on the surface of said one side, said traces collectively lying in and defining a trace surface and being made of a conductive material; and
  at least one of said conductive traces having a three-dimensional conductive circuit feature formed integrally therewith and projecting from said trace surface in a first direction for providing a readily connectable and disconnectable pressure interconnection to another element at said one side of said substrate, said three-dimensional conductive circuit feature consisting essentially of the conductive material of said conductive trace shaped to form a back side depression, and a rigid high strength material filling said depression, one of said traces including a second three-dimensional conductive circuit feature formed integrally therewith and projecting at least partly through said dielectric substrate in a direction opposite said first direction for connection to another element at a second side of said substrate.

2. The circuit of claim 1 wherein said dielectric comprises an electrical connector wafer and wherein a plurality of said traces are formed with integral projecting features, said features defining interconnection sites extending from and above the surface of said dielectric wafer for electrically connecting said traces to a second electrical circuit.

3. A three-dimensional electrical circuit comprising:
  a substrate having first and second sides, and
  a plurality of conductors on said first side having outer surfaces lying in and defining a conductor surface, at least some of said conductors having forward raised contact features integral therewith and projecting in a first direction from said conductor surface away from said substrate for providing a readily connectable and disconnectable pressure interconnection to another element at said first side of said substrate, said contact features and said conductors consisting essentially of a conductive material having poor structural characteristics, at least some of said contact features having a back side depression filled with a contact feature rigidifying high strength material, at least one of said conductors having a rearward raised feature integral therewith and projecting from said conductor surface through said substrate in a direction opposite said first direction for connection to another element at said second side of said substrate.

4. A three-dimensional electrical circuit comprising:
  a substrate having first and second sides, and
  a plurality of conductors on said first side having outer surfaces lying in and defining a conductor surface, at least some of said conductors having contact features integral therewith and projecting from said conductor surface in a first direction for providing a readily connectable and disconnectable pressure interconnection to another element at said first side of said substrate, said substrate having at least one hole there through, and a post feature integrally formed with one of said conductors and projecting through said substrate hole in a direction opposite said first direction for connection to another element at said second side of said substrate.

5. The circuit of claim 3 including a ground shield secured to said second side of said substrate, said rearward raised feature projecting through said substrate into contact with said ground shield to provide a through-the-substrate connection from said ground shield to conductors on said first side of said substrate.

6. The circuit of claim 5 including a first non-conductive coverlay covering said first side of said substrate and said conductors, said coverlay having a hole that receives said forward raised features.

* * * * *